United States Patent [19]

Jenck

[11] 4,431,593

[45] Feb. 14, 1984

[54] ESTER PREPARATION BY CARBONYLATION OF MONOOLEFINS

[75] Inventor: Jean Jenck, Villeurbanne, France

[73] Assignee: Rhone-Poulenc Industries, Paris, France

[21] Appl. No.: 303,947

[22] Filed: Sep. 21, 1981

[30] Foreign Application Priority Data

Oct. 3, 1980 [FR] France ................................ 80 21542

[51] Int. Cl.$^3$ ............................................... C07C 67/38
[52] U.S. Cl. .......................... 260/410.9 R; 260/410.5; 560/187; 560/204; 560/232; 560/233
[58] Field of Search ............... 560/232, 233, 187, 204; 260/410.5, 410.9 R, 410.9 C

[56] References Cited

U.S. PATENT DOCUMENTS

| | | | |
|---|---|---|---|
| 3,322,819 | 5/1967 | Schreyer | 560/204 |
| 3,397,226 | 8/1968 | Fenton | 560/204 |
| 3,507,891 | 4/1970 | Hearne et al. | 260/410.9 C |
| 3,668,249 | 6/1972 | Fenton | 260/546 |
| 3,856,832 | 12/1974 | Solhjell | 560/233 |
| 3,976,670 | 8/1976 | Fanning | 560/233 |
| 3,996,164 | 12/1976 | Matsuda | 260/410.9 C |
| 4,039,572 | 8/1977 | Funakoshi et al. | 560/207 |
| 4,041,057 | 8/1977 | Fanning | 260/410.9 C |
| 4,235,744 | 11/1980 | Pesa et al. | 560/204 |

OTHER PUBLICATIONS

Matsuda A., *Bull. Chem. Soc. Japan*, vol. 46, No. 2, Feb. 1973, pp. 524–530.

*Primary Examiner*—Thomas G. Wiseman
*Assistant Examiner*—Frederick W. Pepper
*Attorney, Agent, or Firm*—Burns, Doane, Swecker & Mathis

[57] ABSTRACT

Organic esters, e.g., linear esters, including diesters, are prepared by carbonylating a monoolefin with carbon monoxide and an alcohol in the presence of a catalytically effective amount of a catalyst comprising cobalt, a tertiary amine base and ruthenium.

18 Claims, No Drawings

ESTER PREPARATION BY CARBONYLATION OF MONOOLEFINS

BACKGROUND OF THE INVENTION

1. Field of the Invention

The present invention relates to the preparation of esters by carbonylating monoolefins, and, more especially, to such carbonylation by reacting carbon monoxide and an alcohol with compounds containing but a single olefinic double bond.

The invention also relates to the preparation of diesters from alkyl pentenoates, and in such respect relates particularly to the synthesis of alkyl adipates by carbonylating alkyl pent-3-enoates.

2. Description of the Prior Art

It is known to this art, from *Bulletin of the Chemical Society of Japan*, Volume 46, pages 526 and 527 (1973), that a mixture containing dialkyl esters, and in particular an alkyl adipate, is obtained by reacting carbon monoxide and an alcohol with an alkyl pent-3-enoate, under high pressure and at elevated temperature, in the presence of cobalt carbonyl and a heterocyclic and aromatic nitrogen-containing base. However, the industrial-scale development of a technique of this type, the value of which is not contested in principle, is greatly compromised by the low activity of the catalyst system used. Cf. U.S. Pat. Nos. 3,397,226 and 3,668,249.

SUMMARY OF THE INVENTION

Accordingly, a major object of the present invention is the provision of an improved process for the preparation of carboxylic acid esters, in enhanced efficiency, via the carbonylation of monoolefins, by reacting carbon monoxide and an alcohol with a monoolefinically unsaturated compound, in the presence of cobalt, a tertiary nitrogen-containing base and ruthenium.

DETAILED DESCRIPTION OF THE INVENTION

More particularly according to the present invention, carbon monoxide and an alcohol R—OH are thus reacted with a compound of the formula $R_1CH=CHR_2$, in which: $R_1$ and $R_2$, which are identical or different, represent hydrogen or an alkyl radical having at most 20 carbon atoms, which can be substituted by one or two chlorine atoms or alkoxy groups containing at most 4 carbon atoms, it also being possible for $R_1$ to represent a radical $-(CH_2)_p-COOH$, $-(CH_2)_p-COOR_3$ or $-(CH_2)_p-CN$, in which p is an integer equal to at most 6, which can be zero, and $R_3$ represents an alkyl radical containing at most 12 carbon atoms, it also being possible for one or two methylene groups to contain an alkyl substituent having at most 4 carbon atoms, and it also being possible for $R_1$ and $R_2$ together to form a single divalent radical $-(CH_2)_q-$, if appropriate containing one or two alkyl substituents having at most 4 carbon atoms, q being an integer between 3 and 6 inclusive, and R is an alkyl radical containing at most 12 carbon atoms, which is optionally substituted by one or two hydroxyl groups, a cycloalkyl radical having from 5 to 7 carbon atoms, an aralkyl radical having from 7 to 12 carbon atoms or a phenyl radical.

The starting materials are conveniently carbonylated in accordance with the present process are thus compounds containing a single internal or terminal olefinic double bond; these compounds more specifically contain from 3 to 20 carbon atoms.

By carrying out the subject process, saturated esters are obtained, namely, compounds which contain, on the one hand, a carboxylate group (—COOR) and, on the other hand, one hydrogen atom more than the starting material. The compound in which the carboxylate group (—COOR) is located in the terminal position on the main chain of the starting material predominates among such esters; hereinafter compounds of this particular type will be designated by the term "linear esters".

A first category of more particularly suitable starting materials has the formula: $R_1CH=CHR_2$ in which $R_1$ and $R_2$, which are identical or different, represent hydrogen or an alkyl radical having at most 10 carbon atoms, or alternatively together form a single divalent radical $-(CH_2)_q-$, q having the above meaning and it being possible for the said radical to contain 1 or 2 methyl substituents, if appropriate. Examples of such compounds are propylene, but-1-ene, but-2-ene, hexenes, octenes and dodec-1-ene.

A second category of more particularly suitable starting materials comprises the compounds of the formula: $R_1CH=CHR_2$ in which $R_1$ represents a radical $-(CH_2)_p-COOR_3$, p and $R_3$ having the above meaning and it being possible for one or two methylene groups to contain an alkyl substituent having at most 4 carbon atoms, and $R_2$ represents hydrogen or an alkyl radical having at most 4 carbon atoms.

Among the compounds of this type, alkyl pentenoates are of very particular value because same make it possible to obtain alkyl adipates, which are adipic acid intermediates.

The present process requires the use of an alcohol of the formula ROH, R having the meaning given above.

The following are exemplary of alcohols which can be used within the scope of the present process: methanol, ethanol, isopropanol, n-propanol, tert.-butanol, n-hexanol, cyclohexanol, 2-ethylhexan-1-ol, dodecan-1-ol, ethylene glycol, hexane-1,6-diol, benzyl alcohol, phenylethyl alcohol and phenol.

It is preferred to use an alkanol having at most 4 carbon atoms; methanol and ethanol are suitable for carrying out the present process.

The alcohol and the monoolefinic compound can be employed in stoichiometric amounts. However, it is preferred to use an excess of alcohol, in a proportion of 1 to 10 or, preferably, 2 to 5 mols of alcohol per mol of monoolefinic compound.

The subject reaction is also carried out in the presence of cobalt. Any source of cobalt capable of reacting with carbon monoxide in the reaction medium to provide cobalt carbonyl complexes in situ can be used within the scope of the present process.

Examples of typical sources of cobalt are finely divided cobalt metal, inorganic salts, such as cobalt nitrate or carbonate, and organic salts, in particular carboxylates. Cobalt carbonyls or hydrocarbonyls can also be employed; dicobalt octacarbonyl is suitable for carrying out the present process.

The molar ratio of the monoolefinic compound to the cobalt is generally between 10 and 1,000. This ratio is advantageously fixed at a value of between 20 and 300.

The process according to the present invention also requires the presence of a tertiary nitrogen-containing base having a $pK_a$ of between 3 and 10.

Preferred are nitrogen-containing heterocyclic compounds comprising 5 to 6 ring members, which can contain one or two substituents selected from among alkyl or alkoxy groups having at most 4 carbon atoms, the hydroxyl group and halogen atoms, which contain 2 or 3 double bonds, if appropriate, and which can furthermore be fused to a benzene nucleus, if appropriate, with the proviso that the links adjacent to the nitrogen hetero-atom are neither substituted nor common to two rings.

Nitrogen-containing heterocyclic compounds with 6 ring members, having a $pK_a$ of between 4 and 7, in particular pyridine, 4-picoline, isoquinoline and 3,5-lutidine, are more particularly preferred for carrying out the present process.

The amount of tertiary nitrogen-containing base employed is typically such that the molar ratio N/Co is between 1 and 50. Preferred is a ratio which ranges from 4 to 25.

One of the essential characteristics of the process according to the invention is the addition of ruthenium to the catalyst system based on cobalt and a tertiary amine. The precise form in which the ruthenium is employed in the reaction is not of critical importance. Triruthenium dodecacarbonyl, and more generally any ruthenium compound capable of providing ruthenium carbonyls, in situ, under the reaction conditions, are particularly suitable for carrying out the invention. In this respect, ruthenium metal in finely divided form, ruthenium carboxylates (in particular, ruthenium acetate), ruthenium halides (in particular, ruthenium trichloride) and ruthenium acetylacetonate are preferred.

The amount of ruthenium to be used is also not critical. The proportion of ruthenium in the reaction medium, which has a favorable influence on the reaction rate, will be determined, in particular, as a function of the rate which it will be considered appropriate to reach. In general, the presence of an amount as low as 0.005 gram atom of ruthenium per gram atom of cobalt leads to appreciable results. In proves undesirable to employ more than 5 gram atoms of ruthenium per gram atom of cobalt. Good results are obtained if the atomic ratio Ru/Co ranges from 0.01 to 2.5 or, preferably, from about 0.1 to 1.

According to the present invention, carbon monoxide and an alcohol (ROH) are thus reacted with a monoolefinic compound, in the presence of the catalyst system defined above. The reaction is carried out in the liquid phase at a temperature above 120° C., no advantage being gained by exceeding 200° C., under a carbon monoxide pressure which is at least 50 bars and can be as much as 1,000 bars. It is preferred to carry out the reaction at a temperature on the order of 130° to 180° C. and under a carbon monoxide pressure on the order of 100 to 300 bars.

Of course, the optimum pressure and temperature conditions will be the more severe, the less reactive the starting material, and this is the case especially if the degree of steric protection of the double bond increases.

It is possible to use solvents or diluents which are inert under the reaction conditions. Examples of solvents of this type are aliphatic or aromatic hydrocarbons, such as pentane, cyclohexane, benzene and toluene. However, the products of the process or the starting alcohols are entirely suitable solvents or diluents.

Substantially pure carbon monoxide, as available commercially, is used. However, the presence of impurities, such as carbon dioxide, methane or nitrogen, is not harmful; the presence of traces of hydrogen (less than 3% by volume) tends to stabilize the catalyst system.

As indicated hereinabove, the process according to the present invention is preferably applied to the synthesis of diesters from alkyl pentenoates. In general, an alkyl pent-3-enoate is used, although pent-2-enoates, pent-4-enoates and mixtures of alkyl pentenoates can be used. Within the scope of this invention, it proves preferable to select the alcohol (co-reactant) corresponding to the alkyl radical of the starting ester, the alkyl radical advantageously having at most 4 carbon atoms. Good results are obtained starting from one or the other of the following pairs of reactants: methyl pentenoate and methanol, and ethyl pentenoate and ethanol.

If the reaction is carried out with a high concentration of cobalt, namely, with a molar ratio of the alkyl pentenoate to the cobalt situated within the range from about 10 to 50, in order to obtain a high proportion of linear diester (adipate), it proves preferable to limit the atomic ratio Ru/Co to a value ranging from 0.01 to 0.25, the molar ratio N/Co being fixed at a value ranging from about 3 to 6.

If the reaction is carried out with a low concentration of cobalt, namely, with a molar ratio of the monoolefinic compound to the cobalt ranging from about 150 to 350, in order to obtain a high proportion of adipate, it proves preferable to fix the atomic ratio Ru/Co at a value ranging from about 0.25 to 1 and to increase the molar ratio N/Co to a value ranging from about 8 to 25.

In this preferred embodiment, the presence of traces of hydrogen on the order of at most 1% of the volume of the carbon monoxide has a particularly favorable effect on the course of the reaction.

In order to further illustrate the present invention and the advantages thereof, the following specific examples are given, it being understood that same are intended only as illustrative and in nowise limitative.

EXAMPLES

In said examples which follow, the following conventions were used:

The compounds resulting from the position isomerization of the olefinic double bond were not included in the products formed.

=/Co: denotes the molar ratio of the monoolefinic compound (starting material) to the cobalt;

DC (%): denotes the number of mols of products formed per 100 mols of starting material introduced;

RT (%): denotes the number of mols of esters per 100 mols of products formed;

S (%): denotes the number of mols of linear ester per 100 mols of esters formed, which is commonly referred to as the degree of linearity;

Ru(acac)$_3$: denotes ruthenium acetylacetonate;

Ru(OAc)$_3$: denotes ruthenium acetate;

T (°): denotes the temperature in degrees centigrade;

t: denotes the duration of an experiment at the temperature indicated, expressed in hours;

A: denotes the activity expressed in mols of products formed per hour and per gram atom of cobalt;

X (%): denotes the number of mols of diesters per 100 mols of products formed;

Y (%): denotes the number of mols of alkyl adipate per 100 mols of products formed; and Z (%): denotes the number of mols of alkyl pentanoate per 100 mols of products formed.

Examples 1 to 6

Table I which follows summarizes the particular conditions utilized for and also the results obtained in a series of experiments involving the carbonylation of hex-1-ene. The procedure used was as follows:

Hex-1-ene, dicobalt, octacarbonyl, triruthenium dodecacarbonyl, methanol and isoquinoline (unless otherwise indicated) were introduced into a 125 cm$^3$ stainless steel autoclave purged under a stream of argon. The autoclave was then purged with a stream of carbon monoxide containing 0.7% by volume of hydrogen, and was then heated to the temperature indicated in Table I below, under a pressure of 130 bars.

After a reaction time of two hours at this temperature, the autoclave was cooled and degassed. The reaction mixture was then analyzed by gas phase chromatography.

Control experiments a, b and c, also shown in Table I, were carried out in the absence of ruthenium.

TABLE I

| Example No. | Hex-1-ene (mmols) | Methanol (mmols) | Cobalt (mg atoms) | =/Co | N/Co | Ru/Co | T (°C.) | DC (%) | RI (%) | S (%) |
|---|---|---|---|---|---|---|---|---|---|---|
| a (x) | 103 | 500 | 4.0 | 26 | 21 | 0 | 150 | 23 | ND | 82 |
| 1 (x) | 100 | 500 | 4.0 | 25 | 22 | 0.5 | 150 | 61 | ND | 81 |
| 2 (xx) | 100 | 502 | 4.0 | 25 | 22 | 0.1 | 150 | 57 | 100 | 76 |
| b | 101 | 303 | 1.92 | 53 | 4.3 | 0 | 130 | 27 | 100 | 83 |
| 3 | 100 | 301 | 1.90 | 53 | 4.2 | 0.1 | 130 | 42 | 100 | 86 |
| 4 | 100 | 300 | 2.00 | 50 | 4.1 | 0.33 | 130 | 39 | 100 | 85 |
| 5 | 101 | 304 | 1.90 | 53 | 4.3 | 1.05 | 130 | 36 | 100 | 86 |
| c | 80 | 200 | 2.80 | 28 | 4.2 | 0 | 160 | 18 | 98.7 | 83 |
| 6 | 66 | 198 | 2.60 | 25 | 4.2 | 0.25 | 160 | 48 | 96.0 | 75 |

(x) experiment carried out with pyridine, under 150 bars, for 1 hour.
(xx) experiment carried out with ethanol and pyridine, under 150 bars, for 1 hour.
ND: not determined.

Examples 7 to 12

Table II which follows summarizes the particular conditions utilized for and also the results obtained in a second series of experiments carried out employing various monoolefinic compounds and in accordance with the procedure described above, the cobalt being employed in the form of dicobalt octacarbonyl, unless otherwise indicated.

Control experiment d, also shown in Table II below, was carried out in the absence of ruthenium.

TABLE II

| Example No. | Substrate (mmols) | Alcohol (mmols) | Cobalt (mg atoms) | Base | Ruthenium | =/Co | N/Co | Ru/Co | P (bars) | T t | DC (%) | RT (%) | S (%) |
|---|---|---|---|---|---|---|---|---|---|---|---|---|---|
| d (x) | hex-3-ene 83.3 | methanol 154 | 2 | 4-picoline | — | 42 | 4.0 | 0 | 130 | 135° C. 2 hrs. | 0 | — | — |
| 7 (x) | hex-3-ene 101 | methanol 150 | 2 | 4-picoline | Ru$_3$(CO)$_{12}$ | 51 | 3.9 | 2.3 | 130 | 135° C. 2 hrs. | 75 | 100 | 83 |
| 8 | tetradec-1-ene 100 | methanol 501 | 0.96 | 3,5-lutidine | Ru(acac)$_3$ | 104 | 8.4 | 2 | 130 | 160° C. 16 hrs. | 48 | 98.6 | 68 |
| 9 | cyclo-hexene 100 | ethanol 298 | 1.98 | isoquino-line | RuCl$_3$ | 50.5 | 12.1 | 0.25 | 200 | 190° C. 2 hrs. | 67 | 99.3 | 100 |
| 10 | dodec-1-ene 100 | ethanol 499 | 4.0 | pyridine | RuCl$_3$ | 25 | 22 | 0.50 | 150 | 150° C. 1 hr. | 23 | 100 | 80 |
| 11 | hex-2-ene 100 | ethanol 498 | 4.0 | pyridine | Ru(acac)$_3$ | 25 | 22 | 0.50 | 150 | 150° C. 1 hr. | 11 | 100 | 69 |
| 12 (xx) | pent-3-ene-nitrile 100 | methanol 148 | 2.04 | 4-picoline | Ru$_3$(CO)$_{12}$ | 49 | 4.0 | 0.15 | 130 | 160° C. 4 hrs. | 44 | 78.3 | 78 |

(x) experiment carried out with cobalt carbonate, in 10 cm$^3$ of toluene.
(xx) experiment carried out in 10 cm$^3$ of ethyl propionate.

Examples 13 to 16

100 mmols of alcohol (the nature of which being specified in Table III below), 50 mmols of the corresponding alkyl pent-3-enoate, 1 mmol of dicobalt octacarbonyl, 8 mmols of isoquinoline (the molar ratio N/Co was thus equal to 4) and a ruthenium compound, the nature and the amount introduced of which also being indicated in Table III below, were introduced into a 125 cm$^3$ stainless steel autoclave purged under a stream of argon.

The autoclave was then purged with a stream of carbon monoxide containing 0.7% (by volume) of hydrogen, and was then heated to 160° C. under a pressure of 130 bars. The results obtained in a reaction time of one hour at 160° C. are shown in said Table III.

Control experiments e and f were carried out in the absence of ruthenium.

TABLE III

| Example No. | Alcohol | Ruthenium Nature | mmols | Ru/Co | A | X (%) | Y (%) | Z (%) |
|---|---|---|---|---|---|---|---|---|
| e | ethanol | — | 0 | 0 | 5.6 | 93 | 73.5 | 7 |
| 13 | ethanol | Ru$_3$(CO)$_{12}$ | 0.066 | 0.10 | 12 | 87.8 | 70.0 | 10.3 |
| f | methanol | — | 0 | 0 | 6.8 | 93.2 | 78.0 | 6.8 |

TABLE III-continued

| Example No. | Alcohol | Ruthenium Nature | mmols | Ru/Co | A | X (%) | Y (%) | Z (%) |
|---|---|---|---|---|---|---|---|---|
| 14 | methanol | Ru$_3$(CO)$_{12}$ | 0.022 | 0.035 | 15.1 | 93.1 | 77.0 | 6.4 |
| 15 | methanol | Ru(acac)$_3$ | 0.2 | 0.10 | 15.8 | 92.0 | 76.7 | 7.5 |
| 16 | methanol | Ru(OAc)$_3$ | 0.4 | 0.10 | 14.5 | 90.7 | 75.7 | 8.2 |

This table shows that the addition of a small amount of ruthenium makes it possible to increase the reaction rate without substantially modifying the distribution of the products obtained.

Examples 17 to 24

A series of experiments was carried out, in accordance with the procedure described above, by reacting carbon monoxide containing 0.7% (by volume) of hydrogen with a charge containing 100 mmols of methyl pent-3-enoate, 200 mmols of methanol, dicobalt octacarbonyl, triruthenium dodecacarbonyl and, unless otherwise indicated, isoquinoline. The particular conditions utilized for and also the results obtained in a reaction time of two hours at 160° C., under a pressure of 130 bars, are shown in Table IV below.

Control experiments g and h, also shown in this table, were carried out in the absence of ruthenium.

TABLE IV

| Example No. | Co$_2$(CO)$_8$ (mmols) | Isoquinoline (mmols) | Ru$_3$(CO)$_{12}$ (mmols) | =/Co | N/Co | Ru/Co | A | X (%) | Y (%) | Z (%) |
|---|---|---|---|---|---|---|---|---|---|---|
| g | 0.77 | 6.0 | 0 | 65 | 3.9 | 0 | 6.7 | 93.8 | 79.7 | 5.5 |
| 17 | 0.74 | 6.3 | 0.05 | 67 | 4.3 | 0.1 | 19.2 | 90.6 | 74.6 | 8.3 |
| 18 | 0.79 | 6.9 | 0.13 | 63 | 4.4 | 0.25 | 18.2 | 92.1 | 75.4 | 6.8 |
| 19 | 0.78 | 6.1 | 0.37 | 64 | 3.9 | 0.70 | 21.3 | 86.5 | 67.0 | 12.1 |
| 20 | 0.76 | 6.6 | 0.50 | 66 | 4.3 | 1.00 | 22.6 | 86.2 | 66.7 | 12.1 |
| h | 0.68 | 11.0 | 0 | 74 | 8.1 | 0 | 5.1 | 93.6 | 80.5 | 5.8 |
| 21 | 0.75 | 12.1 | 0.50 | 67 | 8.1 | 1.00 | 18.8 | 86.6 | 69.3 | 12.6 |
| 22 | 0.73 | 17.5 | 0.50 | 69 | 12 | 1.03 | 13.1 | 85.3 | 68.3 | 13.8 |
| 23 (x) | 0.71 | 17.2 | 0.50 | 70 | 12 | 1.06 | 19.4 | 87.4 | 71.4 | 11.6 |
| 24 (x) | 0.72 | 28.8 | 0.12 | 69 | 20 | 0.25 | 11.1 | 92.0 | 77.5 | 7.4 |

(x) experiment carried out with pyridine (as a replacement for isoquinoline).

Examples 25 to 40

A series of experiments was carried out, in accordance with the procedure described above, by reacting carbon monoxide containing 0.7% (by volume) of hydrogen with a charge containing 100 mmols of methyl pent-3-enoate, 200 mmols of methanol, dicobalt octacarbonyl, ruthenium introduced in the form of various compounds, the nature of which being indicated in Table V below, and isoquinoline. The particular conditions utilized for and also the results obtained in a reaction time of two hours at 160° C., under a pressure of 130 bars, are shown in Table V below.

Control experiments i, j and k, also shown in this table, were carried out in the absence of ruthenium.

TABLE V

| Example No. | Co$_2$(CO)$_8$ (mmols) | Ruthenium (nature) | =/Co | N/Co | Ru/Co | A | X (%) | Y (%) | Z (%) |
|---|---|---|---|---|---|---|---|---|---|
| i | 0.20 | — | 245 | 4.8 | 0 | 8.45 | 90 | 69 | 7.5 |
| j | 0.225 | — | 227 | 8.1 | 0 | 8.40 | 91.8 | 75 | 6.6 |
| k | 0.205 | — | 237 | 20.3 | 0 | 1.7 | 90.5 | 71.5 | 9.5 |
| 25 | 0.205 | Ru(acac)$_3$ | 242 | 4.9 | 0.25 | 10.1 | 91.5 | 72.9 | 3.5 |
| 26 | 0.21 | RuCl$_3$.nH$_2$O | 235 | 4.8 | 0.24 | 20.1 | 86.6 | 64.5 | 9.3 |
| 27 | 0.185 | Ru$_3$(CO)$_{12}$ | 265 | 4.5 | 0.27 | 15.4 | 88.7 | 62.2 | 7.7 |
| 28 | 0.21 | Ru$_3$(CO)$_{12}$ | 240 | 8.7 | 0.24 | 18.9 | 92.2 | 72.8 | 6.3 |
| 29 | 0.195 | Ru$_3$(CO)$_{12}$ | 261 | 21.7 | 0.26 | 23.7 | 94.1 | 78.8 | 5.2 |
| 30 | 0.23 | Ru(acac)$_3$ | 213 | 4.3 | 0.86 | 17.1 | 88.2 | 64.8 | 3.2 |
| 31 | 0.225 | Ru$_3$(CO)$_{12}$ | 221 | 4.5 | 0.90 | 21.9 | 86.4 | 57.7 | 10 |
| 32 | 0.21 | Ru$_3$(CO)$_{12}$ | 238 | 5.7 | 0.96 | 23.2 | 89.6 | 63.3 | 7.8 |
| 33 | 0.205 | Ru$_3$(CO)$_{12}$ | 238 | 9 | 0.97 | 28.6 | 90.5 | 67.5 | 7.4 |
| 34 | 0.21 | Ru$_3$(CO)$_{12}$ | 236 | 12 | 0.95 | 31.3 | 91.7 | 72.6 | 7.1 |
| 35 | 0.21 | Ru$_3$(CO)$_{12}$ | 240 | 19.4 | 0.96 | 33.3 | 91.8 | 75 | 7.2 |
| 36 | 0.195 | Ru$_3$(CO)$_{12}$ | 258 | 42.5 | 1.04 | 12.9 | 89.3 | 71.7 | 9.1 |
| 37 | 0.22 | Ru$_3$(CO)$_{12}$ | 228 | 4.1 | 2.5 | 24.2 | 87.5 | 54 | 8.8 |
| 38 | 0.195 | Ru$_3$(CO)$_{12}$ | 253 | 20.9 | 2.6 | 32.7 | 86.4 | 65.7 | 12.5 |
| 39 | 0.215 | Ru$_3$(CO)$_{12}$ | 224 | 40.0 | 2.4 | 14.7 | 88.1 | 65.9 | 8.1 |
| 40 | 0.21 | Ru(acac)$_3$ | 233 | 5.6 | 4.7 | 18.8 | 81.1 | 48.4 | 16.9 |

Table V shows, on the one hand, that, in the absence of ruthenium, an increase in the molar ratio N/Co results in a very distinct decrease in the reaction rate, and, on the other hand, that the addition of ruthenium makes it possible to obtain an increased reaction rate, the proportion of diesters being virtually unchanged, and that an increase in the molar ratio Ru/Co results in a substantial decrease in the proportion of adipate. However, it is also found in the latter case that an increase in the molar ratio N/Co makes it possible to obtain a high proportion of adipate, with an appreciable reaction rate.

Example 41

Using the equipment and procedure described above, carbon monoxide which was free of hydrogen was reacted with a charge comprising:
(i) 100 mmols of methyl pent-3-enoate,
(ii) 200 mmols of methanol, (iii) 2 mmols of dicobalt octacarbonyl,
(iv) 24 mmols of isoquinoline, and
(v) 0.33 mmol of triruthenium dodecacarbonyl.

The results obtained in a reaction time of two hours at 160° C., under a total pressure of 80 bars, were as follows:
A=6.1
X=87.1%
Y=73.4%
Z=12%

Example 42

Using the equipment and procedure described above, carbon monoxide containing about 0.35% (by volume) of hydrogen was reacted with a charge containing:
(i) 100 mmols of methyl pent-3-enoate,
(ii) 500 mmols of methanol,
(iii) 1 mmol of dicobalt octacarbonyl,
(iv) 8 mmols of 4-picoline, and
(v) 0.22 mmol of triruthenium dodecacarbonyl.

The results obtained in a reaction time of two hours at 140° C., under a total pressure of 250 bars, were as follows:
A=10.3
X=95.5%
Y=76.0%
Z=3.5%

Example 43

Using the equipment and procedure described above, carbon monoxide containing about 0.35% (by volume) of hydrogen was reacted with a charge comprising:
(i) 200 mmols of methyl pent-3-enoate,
(ii) 400 mmols of methanol,
(iii) 2 mmols of dicobalt octacarbonyl,
(iv) 24 mmols of isoquinoline, and
(v) 0.33 mmol of triruthenium dodecacarbonyl.

The results obtained in a reaction time of two hours at 180° C., under a total pressure of 80 bars, were as follows:
A=7.2
X=56.6%
Y=39%
Z=41%

Control Experiment 1

Example 43 was repeated in the absence of ruthenium. Virtually no reaction was observed.

Examples 44 and 45

Using the equipment and procedure described above, a series of experiments was carried out by reacting carbon monoxide containing traces of hydrogen, the percentage by volume of which being designated by $H_2$ (%) in Table VI below, with a charge containing 100 mmols of methyl pent-3-enoate, 200 mmols of methanol, dicobalt octacarbonyl, triruthenium dodecacarbonyl and isoquinoline.

The particular conditions and also the results obtained in a reaction time of two hours at 160° C., under a total pressure of 130 bars, are shown in Table VI below.

Control experiments m to p, also shown in this table, were carried out in the absence of ruthenium.

The said table also shows Examples 31 and 35 and control experiment k.

TABLE VI

| Example No. | $Co_2(CO)_8$ (mmols) | Isoquinoline (mmols) | =/Co | $H_2$ (%) | N/Co | Ru/Co | A | X (%) | Y (%) | Z (%) |
|---|---|---|---|---|---|---|---|---|---|---|
| m | 0.22 | 1.80 | 227 | 0 | 4.1 | 0 | ng | ND | ND | ND |
| 44 | 0.22 | 1.80 | 227 | 0 | 4.1 | 1.0 | 19.2 | 93.9 | 72.5 | 6.1 |
| n | 0.22 | 8.80 | 227 | 0 | 20 | 0 | ng | ND | ND | ND |
| 45 | 0.22 | 8.80 | 227 | 0 | 20 | 1.0 | 10.0 | 90.6 | 69.6 | 9.0 |
| p | 0.18 | 1.90 | 278 | 0.7 | 5.2 | 0 | 8.4 | 89.3 | 68.3 | 3.4 |
| 31 | 0.22 | 1.98 | 221 | 0.7 | 4.5 | 0.9 | 21.9 | 86.4 | 57.5 | 10 |
| 35 | 0.21 | 8.15 | 240 | 0.7 | 19.4 | 0.96 | 33.3 | 91.8 | 75 | 7.2 |
| k | 0.21 | 8.5 | 237 | 0.7 | 20.3 | 0 | 1.7 | 90.3 | 71.5 | 9.5 | ng: negligible
ND: not determined

This table confirms the value of adding ruthenium to the reaction medium, in which the cobalt is in a relatively low concentration, including that case where hydrogen is absent.

Examples 46 to 48

A series of experiments was carried out, in accordance with the procedure described previously, by reacting carbon monoxide containing 0.8% (by volume) of hydrogen with a charge containing 50 mmols of methyl pent-3-enoate, methanol, dicobaltoctacarbonyl, rutheniumdodecacarbonyl, isoquinoline and 10 cc of benzene.

The particular conditions utilized for and also the results obtained in a reaction time of two hours at 160° C., under a pressure of 130 bars, are shown in Table VII below.

TABLE VII

| Example No. | $Co_2(CO)_8$ (mmols) | Methanol (mmols) | N/Co | Ru/Co | DC (%) | X (%) | Y (%) | Z (%) |
|---|---|---|---|---|---|---|---|---|
| 46 | 0.93 | 98 | 4.2 | 0.21 | 65.0 | 93.3 | 79.9 | 5.5 |
| 47 | 0.95 | 43 | 4.2 | 0.21 | 44.7 | 93.6 | 78.0 | 5.9 |
| 48 | 2.04 | 100 | 3.9 | 0.10 | 51.6 | 94.2 | 79.6 | 5.8 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of an organic ester comprising carbonylating a monoolefin with carbon monoxide and an alcohol having the structural formula ROH, wherein R is an alkyl radical having up to 12 carbon atoms, a mono- or dihydroxy substituted alkyl radical having up to 12 carbon atoms, a cycloalkyl radical having from 5 to 7 carbon atoms, an aralkyl radical having from 7 to 12 carbon atoms, or a phenyl radical, in the presence of a catalytically effective amount of a catalyst comprising cobalt, ruthenium and a tertiary amine base, said tertiary amine base being a heterocycle having 5 to 6 ring members only one of which is a tertiary nitrogen atom, said heterocycle comprising 2 or 3 double bonds and being unsubstituted or substituted by one or two alkyl or alkoxy substituents having up to 4 carbon atoms, or hydroxyl or halogen substituents, or said heterocycle being fused to a benzene ring, with the proviso that the links adjacent to the nitrogen atom are neither substituted nor common to two rings, the organic ester produced by said process being the major product of said process, said ester being a saturated ester containing one hydrogen atom more than the monoolefin starting material and bearing a carboxylate group —COOR wherein R is defined as above, said ester comprising predominantly linear ester in which the carboxylate group —COOR is located in the position corresponding to the terminal position on the main chain of the monoolefin starting material.

2. The process as defined in claim 1, wherein said monoolefin has the structural formula:

$R_1CH=CHR_2$ wherein $R_1$ and $R_2$, which may be the same or different, each is hydrogen, an alkyl radical having up to 20 carbon atoms, or a mono- or dichloro- mono- or dialkoxy substituted such alkyl radical, said alkoxy substituents having up to 4 carbon atoms, further wherein $R_1$ also may be $-(CH_2)_p-COOH$, $-(CH_2)_p-COOR_3$ or $-(CH_2)_p-CN$ in which p is an integer ranging from 0 to 6, and $R_3$ is an alkyl radical having up to 12 carbon atoms, or a $C_1-C_4$ alkyl substituted such alkyl radical, such substitution being either on one or two of the methylene groups comprising such alkyl radical, and further wherein $R_1$ and $R_2$ may together form a single divalent radical $-(CH_2)_q-$, or a $C_1-C_4$ mono- or dialkyl substituted such divalent radical, with q ranging from 3 to 6.

3. The process as defined by claim 1 or 2, wherein the monoolefin has from 3 to 20 carbon atoms.

4. The process as defined by claim 1 or 2, wherein said monoolefin has the structural formula:

$R_1CH=CHR_2$ wherein $R_1$ and $R_2$, which may be the same or different, each is hydrogen, an alkyl radical having up to 10 carbon atoms, or together form a divalent radical $-(CH_2)_q-$, in which q ranges from 3 to 6, or mono- or dimethylated such divalent radical.

5. The process as defined by claim 1 or 2, wherein said monoolefin has the structural formula:

$R_1CH=CHR_2$ wherein $R_1$ is $-(CH_2)_p-COOR_3$, in which p is an integer ranging from 0 to 6 and $R_3$ is an alkyl radical having up to 12 carbon atoms, or a $C_1-C_4$ alkyl substituted such alkyl radical, such substitution being either on one or two of the methylene groups comprising such alkyl radical, and $R_2$ is hydrogen or an alkyl radical having up to 4 carbon atoms.

6. The process as defined in claim 5, wherein the monoolefin is an alkyl pentenoate.

7. The process as defined by claim 3, wherein the alcohol is an alkanol having up to 4 carbon atoms.

8. The process as defined by claim 1 or 2, wherein the tertiary amine base is a nitrogen-containing heterocycle having 6 ring members and having a $pK_a$ of between 4 and 7.

9. The process as defined by claim 1 or 2, wherein the molar ratio of the monoolefin to the cobalt ranges from 10 to 1,000.

10. The process as defined by claim 9, wherein the molar ratio of alcohol is monoolefin ranges from 1 to 10.

11. The process as defined by claim 10, wherein the molar ratio N/Co ranges from 1 to 50.

12. The process as defined by claim 11, wherein the atomic ratio Ru/Co ranges from 0.005 to 5.

13. The process as defined by claim 12, wherein the atomic ratio Ru/Co ranges from about 0.10 to 1.

14. The process as defined by claim 12, wherein the reaction is carried out in the liquid phase at a temperature between 120° and 200° C., under a carbon monoxide pressure of between 50 and 1,000 bars.

15. The process as defined by claim 14, wherein the reaction is carried out at a temperature between 130° and 180° C., under a carbon monoxide pressure of between about 100 and 300 bars.

16. The process as defined by claim 14, wherein the molar ratio of alkyl pentenoate to cobalt ranges from about 10 to 50, the atomic ratio Ru/Co ranges from 0.01 to 0.25 and the molar ratio N/Co ranges from about 3 to 6.

17. The process as defined by claim 14, wherein the molar ratio of alkyl pentenoate to cobalt ranges from about 150 to 350, the atomic ratio Ru/Co ranges from 0.25 to 1, and the molar ratio N/Co ranges from about 8 to 25.

18. The process as defined by claim 1 or 2, wherein the carbon monoxide contains traces of hydrogen not exceeding 1% (by volume).

* * * * *